United States Patent [19]

Toomey

[11] Patent Number: 5,063,178
[45] Date of Patent: Nov. 5, 1991

[54] FREEZE-DRIED BLOOD GAS SENSOR

[75] Inventor: John C. Toomey, West Worthington, Ohio

[73] Assignee: Medex, Inc., Hilliard, Ohio

[21] Appl. No.: 495,849

[22] Filed: Mar. 19, 1990

[51] Int. Cl.5 .................... G01N 21/64; G01N 31/22; G02B 23/26

[52] U.S. Cl. .............. 422/82.07; 422/82.06; 436/163; 427/2; 427/157; 427/163; 427/238; 128/634; 250/227.23; 359/123

[58] Field of Search ............ 422/82.06, 55, 82.07; 436/163; 435/34; 427/2, 157, 163, 238; 128/634; 250/227.14, 227.23; 350/96.26; 34/5

[56] References Cited

U.S. PATENT DOCUMENTS

| Re. 31,879 | 5/1985 | Lubbers et al. | 69/45 |
|---|---|---|---|
| 3,713,985 | 1/1973 | Astle | 435/34 X |
| 3,957,583 | 5/1976 | Gibson et al. | 435/34 X |
| 4,168,204 | 9/1979 | Williams | 435/34 |
| 4,200,110 | 4/1980 | Peterson et al. | 128/634 |
| 4,540,410 | 9/1985 | Wood et al. | 34/5 X |
| 4,548,907 | 10/1985 | Seitz et al. | 422/82.07 X |
| 4,682,895 | 7/1987 | Costello | 422/82.06 X |
| 4,727,730 | 3/1988 | Boiarski et al. | 128/667 |
| 4,737,343 | 4/1988 | Hirschfeld | 436/163 X |
| 4,803,049 | 2/1989 | Hirschfeld et al. | 436/163 X |
| 4,824,789 | 4/1989 | Yafuso et al. | 422/83 X |
| 4,965,087 | 10/1990 | Wolfbeis et al. | 427/157 X |
| 4,999,306 | 5/1991 | Yafuso et al. | 422/82.06 X |
| 5,006,314 | 4/1991 | Gourley et al. | 422/82.06 X |

FOREIGN PATENT DOCUMENTS 9000572 1/1990 World Int. Prop. O. .......... 436/163

Primary Examiner—Robert J. Warden
Assistant Examiner—Arlen Soderquist
Attorney, Agent, or Firm—Wood, Herron & Evans

[57] ABSTRACT

A blood chemical sensor has a blood gas sensitive dye contained in a hydrogel matrix, the combination of dye and gel being mounted on the end of an optical fiber. The hydrogel is freeze-dried to facilitate packaging and handling.

7 Claims, 1 Drawing Sheet

FREEZE-DRIED BLOOD GAS SENSOR

BACKGROUND OF THE INVENTION

This invention relates to a blood chemical sensor wherein a dye and hydrogel combination are mounted on an optical fiber. The sensor is of the type described in copending U.S. application Ser. No. 07/419,692, filed Oct. 11, 1989, and in U.S. Pat. No. 4,727,730.

The invention has particular application to a microsized sensor of the type described in application Ser. No. 07/419,692. The sensor is mounted on the tip of an optical fiber of about 0.009 inch in diameter. A dye and hydrogel matrix combination is mounted on the tip of the optical fiber. The dye, when excited by a light beam passing through the optical fiber, will fluoresce and the fluorescence will be reflected back through the optical fiber. When that sensor is inserted into the bloodstream of a patient, blood gases or electrolytes will be absorbed into contact with the dye. The quantity of the particular constituent being examined by the sensor in the blood stream will cause a variation in the intensity of the fluorescence. The type of dye, the carrier in which it is bound, and the wavelength or wavelengths of excitation all can be varied to make the sensor selective to a particular constituent of the blood. Principal among these constituents are $O_2$, $CO_2$ and pH.

BRIEF SUMMARY OF THE INVENTION

The present invention is concerned with a sensor in which the dye is bound in a hydrogel. The hydrogel must be maintained in a moist condition. This requires wet storage and wet packaging. Those requirements impose very demanding conditions on the manufacturing, packaging and sterilization of the sensors.

An objective of the present invention has been to eliminate the problems of wet storage, packaging and the like arising out of the use of hydrogels.

This objective of the present invention is attained by freeze-drying the sensor. The freeze-drying of the sensor will take all of the water out and therefore reduce the size of the sensor by one-half or more than one-half. It is therefore important to the attainment of the objective that the sensor be mounted to the optical fiber in such a way that the shrunken sensor will not become dislodged from the optical fiber.

When the sensor is to be used, it can be reconstituted by exposure to water. It has been found that upon being reconstituted, the sensor does not materially lose any of the sensitivity that it had prior to the freeze-drying process.

There are several advantages to be obtained from the freeze-drying of the sensor. The sensor avoids the difficult and costly technical and FDA regulatory issues on handling (in manufacturing) sterile solution and maintaining the sterility of wet packaging. Dry packaging also avoids the messiness that wet packaging imposes upon the user.

The freeze-dried sensor apparently will permit the use of ethylene oxide (ETO) sterilization. That is not possible with wet storage since the ETO gas will contact the liquid and turn into nonsterilizing and dangerous byproducts such as ethylene glycol.

The freeze-dried sensor further permits the use of plastic optical fibers which are more flexible and less expensive than glass fibers. Plastic fibers are compatible with ETO sterilization, while the alternative sterilization methods of gamma or electron beam irradiation and steam sterilization, required for wet hydrogels, permanently damage the plastic fibers.

BRIEF DESCRIPTION OF THE DRAWINGS

The several features of the present invention will become more readily apparent from the following detailed description taken in conjunction with the accompanying drawings in which.

DETAILED DESCRIPTION OF THE INVENTION

Figure 1:
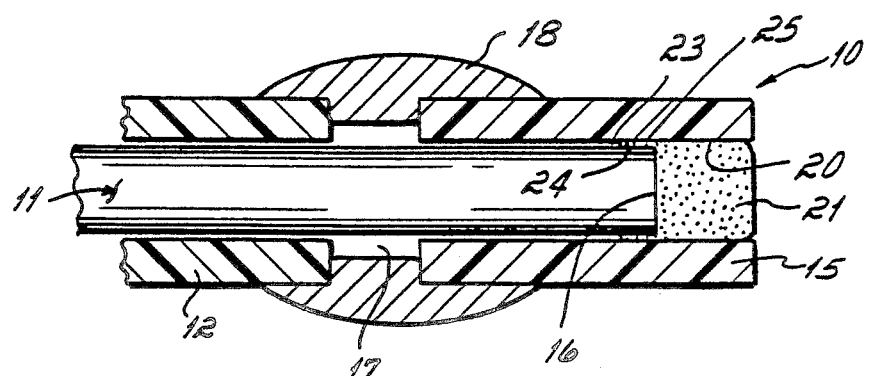
FIG. 1 is a cross-sectional view of a sensor mounted on the end of an optical fiber.

Referring to FIG. 1, there is depicted a sensor 10 that is the type disclosed in application No. 419,692. An optical fiber 11 is clad in a jacket 12. A slidable sleeve 15 surrounds the fiber 11 at its end 16. There is a gap 17 between the jacket 12 and the sleeve 15. That gap is enclosed by applying a cyano acrylate 18 to it.

The sleeve 15 creates a cylindrical chamber 20 beyond the end 16 of the optical fiber. That cylindrical chamber is filled with the sensor matrix liquid mixture. In one form of the invention, the indicator or dye is a fluorescent HOPSA-derivative. It is bound in an acrylamide hydrogel solution. Specific details of the system are set forth in the copending application Ser. No. 07/419,692, the disclosure for which is incorporated herein.

As set forth in that application, the combined hydrogel and HOPSA dye 21 are captured in the sleeve by first depositing a drop of the combination on the end of the optical fiber when the sleeve is positioned against the jacket 12 so that the end of the sleeve and the end of the optical fiber are substantially coextensive. With the drop in that position, the optical fiber 11 is withdrawn from the sleeve 15 to the position indicated in FIG. 1. The fiber 11 acts as a piston creating a vacuum which withdraws the hydrogel dye combination into the recess or cylindrical chamber 20 created by the sleeve's extending beyond the tip of the optical fiber. It is believed that, in the process, the capillary action causes the gel/dye combination to move slightly into the cylindrical space 23 created between the cylindrical wall 24 of the fiber and the cylindrical wall section 25 of the sleeve 15.

The sensor is then subjected to a freeze-drying process. In general, conventional freeze-drying technology is applied, such as the technology described in "A Guide to Freeze Drying for the Laboratory" published by Labconco Corporation.

In accordance with the present invention, the freeze-drying steps applied are as follows:

The sample is frozen by subjecting it to minus 40° C. for one to two hours.

The condenser wall in the dryer is cooled to −40° C. for one to one and one-half hours. A vacuum of 50 to 100 $\mu$ of mercury, preferably about 80 $\mu$.

The shelf temperature is raised to about −10° C.

The sensor is dried for 20 to 24 hours.

The vacuum is shut down, the samples are removed and packaged in hermetically-sealed packaging to avoid being exposed to humidity in the air.

Figure 2:
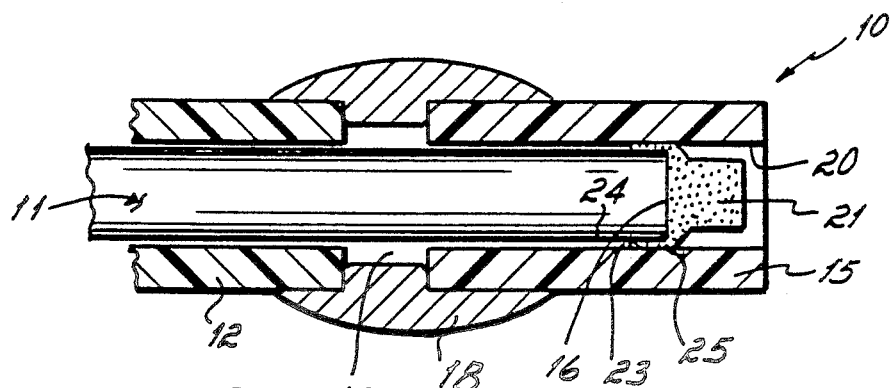
FIG. 2 is a cross-sectional view of the sensor of FIG. 1 in which the fiber has been dehydrated.

The sensor after the freeze-drying process appears as depicted in FIG. 2. It should be noted that it remains attached to the optical fiber probably because of the capillary flow into the space at 23 between the fiber 11 and sleeve 15. Because of the very considerable shrinking as depicted in FIG. 2, it is important that the fiber remain attached in some fashion.

When the sensor is to be used by inserting it into a patient, distilled water is applied to the freeze-dried hydrogel in the recess 20. In one to five minutes, rehydration rapidly occurs. The re-hydrated sensor has substantially the same sensitivity as a sensor that has not been subjected to the freeze-drying process. Further, it returns to the appearance depicted in FIG. 1.

From the above disclosure of the general principles of the present invention and the preceding detailed description of a preferred embodiment, those skilled in the art will readily comprehend the various modifications to which the present invention is susceptible. Therefore, I desire to be limited only by the scope of the following claims and equivalents thereof:

I claim:

1. The method of forming a blood chemical sensor comprising the steps of:

combining a dye and hydrogel, mounting said combined dye and hydrogel on the end of an optical fiber, freeze drying the combined dye and gel.

2. The method as in claim 1 further comprising the step of reconstituting the combined dye and gel by subjecting it to water.

3. The method of forming a blood chemical sensor comprising the steps of:

combining a dye and hydrogel, slidably mounting a sleeve on the end of an optical fiber, mounting said dye and hydrogel on the end of said optical fiber with said sleeve projecting beyond the end of said optical fiber to form a cylindrical chamber that receives said dye and hydrogel, causing a portion of said dye and hydrogel to flow into an annular space between said optical fiber and said sleeve, and freeze drying said dye and hydrogel combination.

4. A blood chemical sensor comprising:

an optical fiber, a dye and hydrogel combination mounted on the end of the optical fiber, said dye and hydrogel combination being freeze-dried.

5. The sensor as in claim 4 in which the optical fiber is a plastic material.

6. A sensor as in claim 4 further comprising:

a sleeve surrounding the end of the optical fiber and projecting therefrom to create a cylindrical chamber that contains said dye and hydrogel combination, said dye and hydrogel combination adhering to an annular space between said sleeve and said optical fiber at the joint between the tip of said optical fiber and said sleeve.

7. A blood probe comprising:

an optical fiber having two ends, one of which is a distal end, a cylindrical sleeve surrounding said fiber and extending beyond said distal end of said fiber, thereby creating a receptacle at the distal end of said fiber, a sensitive dye bound in a cured gel disposed in said receptacle and in intimate contact with the distal end of said optical fiber and free of oxygen at the interface between said dye and the distal end of said fiber, said dye being exposed at the end of said sleeve for contact with blood, said gel and dye being freeze-dried.

* * * * *